US006616631B2

(12) United States Patent
Takagi et al.

(10) Patent No.: US 6,616,631 B2
(45) Date of Patent: Sep. 9, 2003

(54) SAFETY INDWELLING NEEDLE (75) Inventors: Hiroshi Takagi, Yokohama (JP); Kentaro Takemae, Kawasaki (JP)

(73) Assignees: Mitsubishi Pencil Kabushiki Kaisha, Tokyo (JP); Nipro Corporation, Osaka (JP)

( * ) Notice: Subject to any disclaimer, the term of this patent is extended or adjusted under 35 U.S.C. 154(b) by 0 days.

(21) Appl. No.: 10/089,707

(22) Filed: Mar. 29, 2002

(65) Prior Publication Data

US 2002/0156422 A1 Oct. 24, 2002

(30) Foreign Application Priority Data

Jul. 12, 2000 (JP) ....................... 2000-211726
Nov. 17, 2000 (JP) ....................... 2000-350646

(51) Int. Cl.[7] ............................................. A61M 5/00
(52) U.S. Cl. ....................................................... 604/110
(58) Field of Search ........................... 604/110, 164.08, 604/162, 263, 192, 198

(56) References Cited

U.S. PATENT DOCUMENTS

| | | | | |
|---|---|---|---|---|
| 4,747,831 A | | 5/1988 | Kulli ............................ 604/110 |
| 4,813,426 A | * | 3/1989 | Haber et al. ................ 128/763 |
| 4,917,669 A | | 4/1990 | Bonaldo ...................... 604/164 |
| 4,994,042 A | * | 2/1991 | Vadher ........................ 604/165 |
| 5,104,386 A | * | 4/1992 | Alzain ......................... 604/232 |
| 5,279,579 A | * | 1/1994 | D'Amico ..................... 604/192 |
| 5,279,590 A | * | 1/1994 | Sinko et al. ................. 604/263 |
| 5,312,359 A | * | 5/1994 | Wallace ....................... 604/164 |
| 5,360,408 A | * | 11/1994 | Vaillancourt ................. 604/198 |
| 5,383,863 A | * | 1/1995 | Mardones .................... 604/198 |
| 5,411,487 A | * | 5/1995 | Castagna ..................... 604/198 |
| 5,472,430 A | * | 12/1995 | Vaillancourt et al. ........ 604/198 |
| 5,591,138 A | * | 1/1997 | Vaillancourt ................. 604/263 |
| 5,795,336 A | * | 8/1998 | Romano et al. ............. 604/192 |
| 6,077,253 A | * | 6/2000 | Cosme ........................ 604/263 |
| 6,080,137 A | | 6/2000 | Pike ............................ 604/263 |
| 6,325,781 B1 | * | 12/2001 | Takagi et al. ................ 604/110 |

FOREIGN PATENT DOCUMENTS

| | | | |
|---|---|---|---|
| JP | 2000-167051 | 6/2000 | ............ A61M/5/32 |
| JP | 2000-185096 | 7/2000 | .......... A61M/5/158 |

* cited by examiner

Primary Examiner—Sharon Kennedy
(74) Attorney, Agent, or Firm—Darby & Darby (57) ABSTRACT A holder sleeve (1) incorporates an urging means (8) for urging an inner needle (12) to the proximal end side and an actuator (6) which engages the inner needle (12) at the near distal end portion of the holder sleeve (1) so that the inner needle (12) can be released and the tip of the inner needle is projected from the holder sleeve (1). This actuator (6) has an inner needle hub (12a) fixed at the front end thereof and is formed with an actuating member (6a) projected outside the holder sleeve (1). The holder sleeve (1) has a slit (2) which extends to the proximal end side so as to allow the actuating member (6a) of the actuator (6) to slide and assures the path of movement of the actuator (6) released from the near distal end portion of the holder sleeve (1). The inner needle (12) is adapted to be released from the holder sleeve (1) when the actuating member (6a) is moved away from the holder sleeve (1) within the same plane that includes the axis of the holder sleeve (1).

4 Claims, 9 Drawing Sheets

SAFETY INDWELLING NEEDLE

TECHNICAL FIELD

The present invention relates to a safety indwelling needle comprised of a soft outer needle to be inserted and placed within a blood vessel and a hard inner needle which is fitted in the outer needle and pierces the skin of a patient to introduce the outer needle into a blood vessel.

BACKGROUND ART

As a known method for infusing a medical fluid or the like into a patient, an outer needle (catheter) is inserted and placed in the human body to infuse the fluid through this outer needle. As a device for guiding the outer needle, indwelling needles have been known to insert and place the outer needle using the inner needle fitted in the outer needle.

The inner needle is discarded after placement of the outer needle in the human body, but it takes a certain time before the inner needle is discarded. Therefore, if an indwelling needle has no safety mechanism there is a risk of pricking the fingers etc. of health care workers by the inner needle during this period or a so-called needlestick accident occurring. If the patient is infected with the HIV virus or the like, there is a risk that the health care worker might catch the virus or the like from a needlestick accident.

In order to solve this problem, many types of safety indwelling needles which avoid needlestick injuries by covering the inner needle immediately after use have been developed. For example, Japanese Patent Application Laid-Open Hei 3 No.15481 offers a cannula inserting device for retracting a needle hub, which might cause a needlestick, into a hollow handle by means of an urging means.

Alternatively, Japanese Patent Application Laid-Open No.2000-167051, Japanese Patent Application Laid-Open No.2000-185096 etc. present technologies relating to a safety indwelling needle (puncture device) having a retracting mechanism for retracting the inner needle immediately after use into the holder sleeve. These technologies present techniques whereby the inner needle is retracted by means of an urging means when an actuating element is operated in a peripheral direction of the holder sleeve so that the actuating element is fixed to a cutout formed in the holder sleeve.

However, since the device disclosed in Japanese Patent Application Laid-Open 3 No.15481 is constructed so that the mechanism will be released by pressing an element corresponding to a trigger inwardly from the outside of the holder cylinder, this configuration frequently causes wrong actuation such that the trigger is pressed erroneously and the inner needle is retracted when it shouldn't.

On the other hand, the safety indwelling needles disclosed in Japanese Patent Application Laid-Open No.2000-167051, Japanese Patent Application Laid-Open No.2000-185096 etc., are free from the problem of the wrong actuation due to unintended pressing, but these configurations need an actuation in the peripheral direction of the holder sleeve after retraction of the inner needle. Therefore, there is the problem with the devices which causes difficulties in handling, depending on the left or right handedness. In order to solve this problem, two types of products for left and right handedness need to be prepared, which increases in the cost of manufacture and management, and also forces the users to select one from these two types.

The present invention has been devised under the above circumstances, it is therefore an object of the present invention to provide a technology for a safety indwelling needle which is almost never erroneously actuated and free from the problem of the actuation depending on the handedness.

DISCLOSURE OF INVENTION

In order to attain the above object, the present application provides the invention having the following configurations.

The present invention is directed to a safety indwelling needle, comprised of a soft outer needle to be inserted and placed within a blood vessel, a hard inner needle, with an inner needle hub, which is fitted in the outer needle, pierces the skin of a patient to introduce the outer needle into the blood vessel and a holder sleeve having an open distal end and a closed proximal end and capable of holding the inner needle, characterized in that: the holder sleeve incorporates an urging means f or urging the inner needle toward the proximal end side and an actuator which engages the inner needle at a near distal end portion of the holder sleeve so that the inner needle can be released and a tip of the inner needle is projected from the holder sleeve; the actuator has an inner needle hub fixed at a front end thereof and is formed with an actuating member projected outside the holder sleeve; the holder sleeve has a slit which extends to the proximal end side of the sleeve so as to hold and allow the actuating member of the actuator to slide and assures the path of movement of the actuator released from the near distal end portion of the holder sleeve; and the inner needle is adapted to be released from the holder sleeve when the actuating member is moved away from the holder sleeve within a same plane that includes the axis of the holder sleeve.

The inner needle (12) is a hard needle provided with an inner needle hub (12a) at the proximal end thereof. It is usually a metal, mostly made of stainless steel. The tip of the inner needle (12) is beveled in order to facilitate puncture.

The outer needle (11) is placed into the human body after puncture and usually formed of a flexible resin.

The holder sleeve (1) is usually formed of a translucent resin or the like. When the inner needle (12) is punctured into the human body, the blood passes through the inner needle (12) and reaches the inner needle hub (12a). Formation of these portions with a translucent material allows for confirmation of the blood reaching the inner needle hub (12a), hence makes possible visual recognition that the inner needle (12) has reached a blood vessel.

The inner diameter of the holder sleeve (1) is set greater than the inner needle hub (12a) and set smaller than the proximal part of the outer needle (11) or the outer needle hub (11a), so that the inner needle (12) can be retracted thereinto but the outer needle (11) will not be retracted.

The holder sleeve (1) incorporates an actuator (6) which engages an inner needle (12) at the near distal end portion of the holder sleeve (1) so that the inner needle (12) can be released and the tip of the inner needle is projected from the holder sleeve (1). An inner needle hub (12a) is fixed to this actuator (6). An actuating member (6a) is formed so as to project outside the holder sleeve (6). The holder sleeve (1) has a slit (2) which extends toward the proximal end side so as to hold and allow this actuating member (6a) to slide and assures the path of movement of the actuator (6) released from the near distal end portion of the holder sleeve (1).

As the urging means, string-like rubber (not shown), etc., may be employed other than a coil spring (8) which contracts when no load is applied.

The movement path of actuation is adapted to be included in the same plane that includes the axis of the holder sleeve (1). Hence, the problem due to the handedness can be eliminated, differing the case where the actuation is made by the rotational movement about the axis of holder sleeve In the position in which the inner needle (12) is fixed by the actuator (6) at the near distal end portion of the holder sleeve (1) so that the inner needle (12) can be released and the needle tip is projected from the holder sleeve (1), the inner needle (12) and outer needle (11) are punctured into the skin of a patient. When the inner needle (12) and outer needle (11) have reached a blood vessel, the flow of blood through the blood vessel is stopped by hand while the holder sleeve (1) on another hand is pulled away from the patient so as to withdraw the inner needle (12) from the blood vessel. Then the actuating member (6a) of actuator (6) is operated so as to release the actuator (6) from the near distal end portion of the holder sleeve (1). In response to this, the inner needle (12) is urged toward the proximal end side of holder sleeve (1) by the urging means (8), so that the inner needle (12) moves, which is followed by the actuator (6) moving along the slit(2). On the contrary, the outer needle (11) will not retract into the holder sleeve (1) but remains at the set position, so as to be connected to an infusion tube, etc.

The inner needle (12) to move toward the proximal end side of the holder sleeve (1) is moved and held until its tip is completely withdrawn into holder sleeve (1). Since the retracted inner needle (12) is pulled by the coil spring (8) which contracts when no load is applied, the inner needle (12) will not be exposed outside, whereby it is possible to prevent occurrence of needlestick injuries.

In the present invention, for releasing the engagement by shifting the actuating member (6a) away from the holder sleeve, a structure for directly lifting the actuating member (6a) from the holder sleeve (1) is adopted. When the actuating member (6a) is moved away from the holder sleeve (1), the engagement between the holder sleeve (1) and inner needle (12) is released, whereby the inner needle (12) is withdrawn into the holder sleeve (1) by virtue of the coil spring (8). This action, differing from a depressing action, almost never causes an erroneous actuation.

Further, it is preferred that the actuating member has an engagement projection which can be fitted into an engagement window formed in the near distal end portion of the holder sleeve, and the actuator is fixed at the near distal end portion of the holder sleeve when the engagement projection is fitted in the engagement window, and the engagement between the actuator and holder sleeve is released when the engagement projection is pulled up from the engagement window.

According to this configuration, the actuating member (6a) of the actuator (6) is formed with an engagement projection (6b) while an engagement window (3) is formed at the front part of the holder sleeve (1). When this engagement projection (6b) is fitted into the engagement window (3), the actuator (6) is engaged with the holder sleeve (1), and the engagement between the actuator (6) and holder sleeve (1) is released when the engagement projection (6b) is pulled up from the engagement window (3). Therefore, the engaged state can be released by moving the actuating member (6a) of the actuator (6) away from the holder sleeve (1), hence this action, differing from a depressing action, almost never causes an erroneous actuation. When the engaged state between the holder sleeve (1) and actuating member (6a) is released, the inner needle (12) fixed to actuator (6) is retracted into the holder sleeve (1) by virtue of the coil spring (8).

It is also preferred that the actuating member is formed to be flexible and is joined to the actuator by a joint rod which is located closer to the proximal end side than the engagement projection is.

In the present invention, since the actuating member (6a) is formed to be flexible and is joined to the actuator (6) by joint rod (6c) which is located closer to the proximal end side than the engagement projection is, this facilitates smooth actuation. Illustratively, when the outer needle (11) is placed into the human body, the outer needle (11) is slightly pushed out by the second digit of the right hand, for example, so as to separate the outer needle (11) from the inner needle (12). At this moment, the second digit is located around an aftermentioned cutout portion (1f) of the holder sleeve (1). Therefore, the second digit is present slightly forwards with respect to the actuating member (6a). This allows the second digit to raise the actuating member (6a) immediately when the inner needle (12) needs to be retracted.

It is also preferred that a lift abutment (6d) on which the finger is abutted when the engagement projection (6b) is pulled up from the engagement window (3) is provided at the distal end portion of the actuating member (6a).

If no lift abutment (6d) for raising the actuating member (6a) is formed, this obstructs quick retraction of the inner needle (12). This is why a lift abutment (6d) is provided at the front part of the actuating member (6a) in the present invention, whereby a quicker and more reliable retraction of the inner needle (12) can be made.

Figure 4:
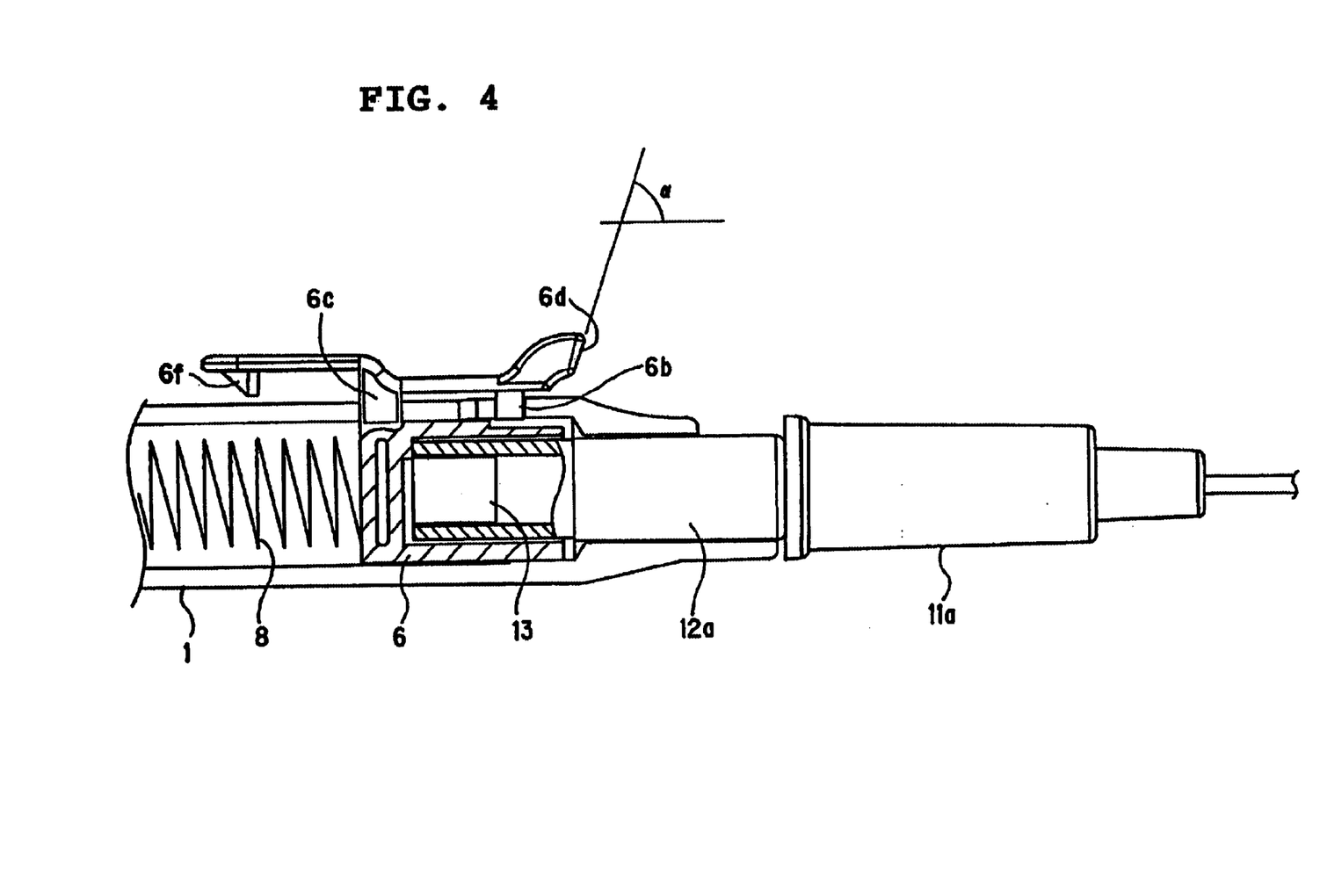
FIG. 4 is an enlarged, partially sectional view showing an actuating member and thereabout according to the first embodiment.

It is preferred that the lift abutment (6d) is formed on the surface facing to the front as is shown in FIG. 4. It is also preferred that the angle a between the axis and the lift abutment (6d) is set at 90 degrees or smaller because this makes it possible for the lift abutment (6d) to hook the finger reliably.

Moreover, it is preferred that anti-slip such as serration is formed because this also enables quick reliable retraction of the inner needle (12).

BEST MODE FOR CARRYING OUT THE INVENTION

The embodiment will be described.

Figure 1:
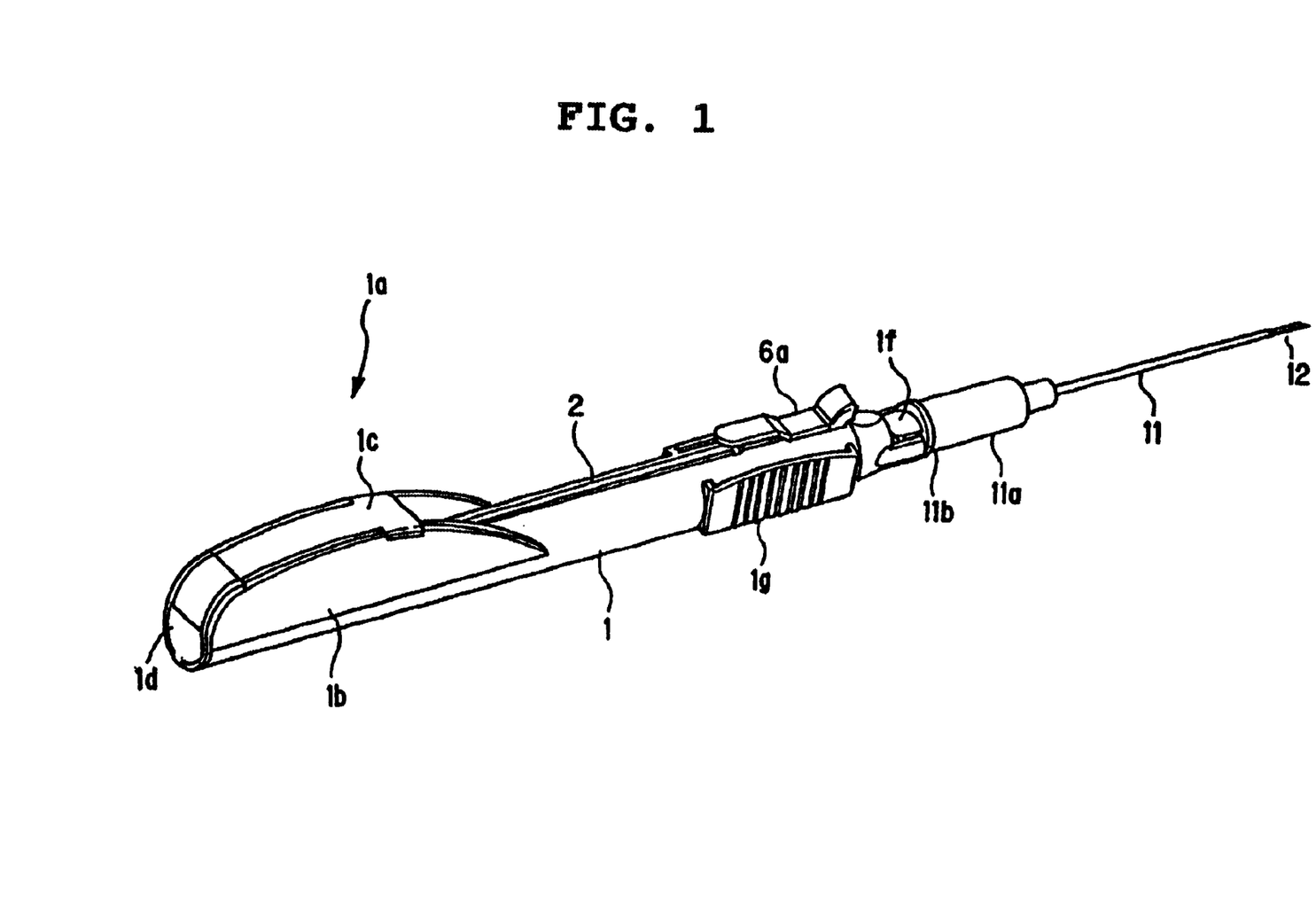
FIG. 1 is an overall perspective view showing an example of a safety indwelling needle injector of the present invention.
Figure 2:
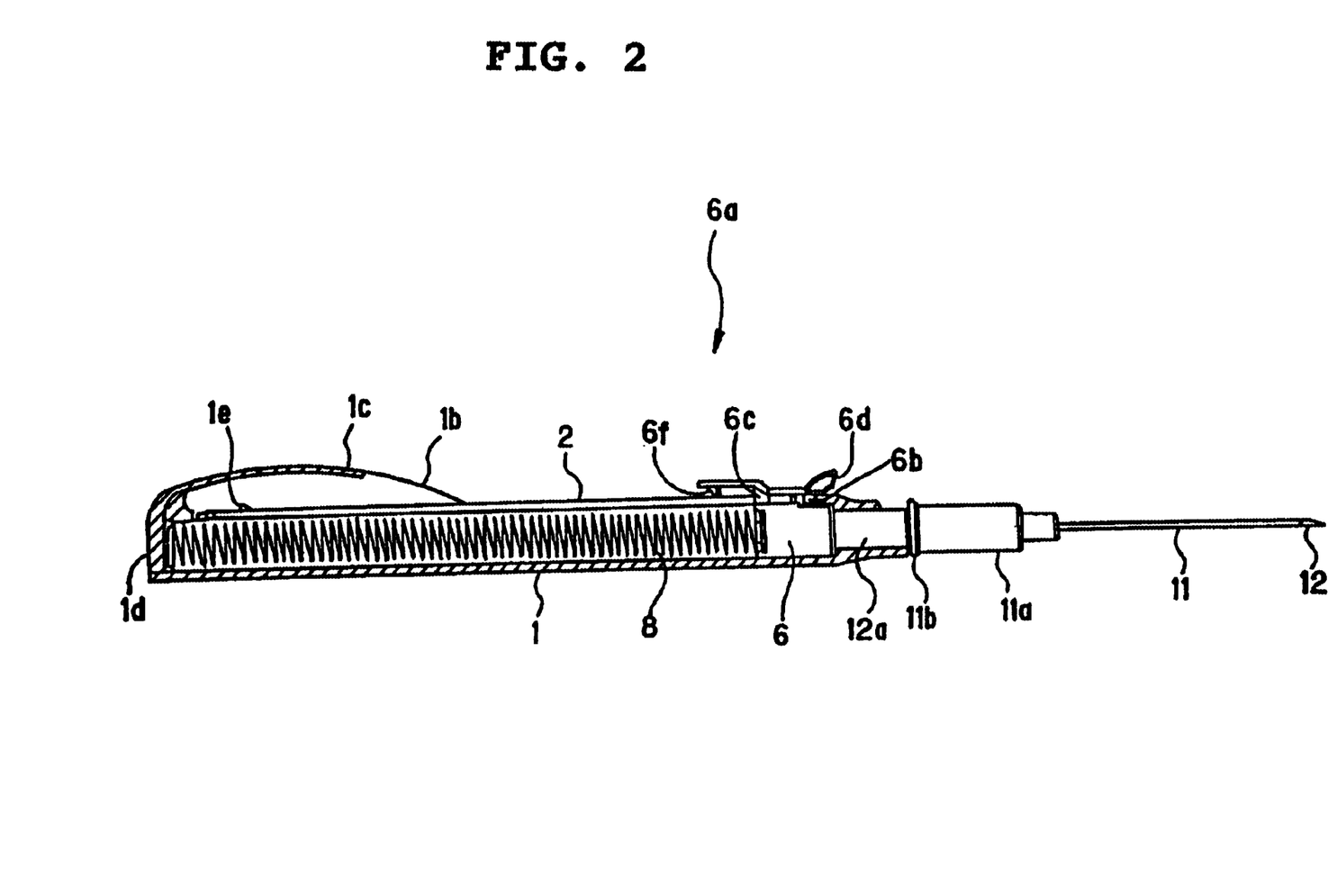
FIG. 2 is a partially sectional vertical view showing a safety indwelling needle injector before use, according to the present invention.

FIGS. 1 and 2 show a safety indwelling needle comprised of a soft outer needle 11 to be inserted and placed within a blood vessel, a hard inner needle 12, with an inner needle hub 12a, which is fitted in the outer needle 11 and pierces the skin of a patient to introduce the outer needle 11 into a blood vessel, and a holder sleeve 1 which has an open distal end and closed proximal end and is capable of holding inner needle 12. This safety indwelling needle is adapted to enclose inner needle 12 after puncture up to the needle tip thereof.

Holder sleeve 1 incorporates an urging means 8 for urging inner needle 12 toward the proximal side and an actuator 6 which engages inner needle 12 at the near distal end portion of holder sleeve 1 so that inner needle 12 can be released and the tip of the inner needle is projected from holder sleeve 1.

Actuator 6 has inner needle hub 12a fixed at the front end thereof and is formed with an actuating member 6a projected outside holder sleeve 1.

Formed in holder sleeve 1 is a slit 2 which extends toward the proximal side of the sleeve so as to hold and allow actuating member 6a of actuator 6 to slide and assures the path of movement of the actuator 6 released from the distal end portion of holder sleeve 1. Thereby, inner needle 12 is adapted to be released from holder sleeve 1 when actuating member 6a is moved away from holder sleeve 1 within the same plane that includes the axis of holder sleeve 1.

A stopper mechanism 1a for arresting inner needle 12 having been moved to the proximal side of holder sleeve 1 is provided at the near proximal end portion of holder sleeve 1.

The stopper mechanism 1a is to protect actuating member 6a of actuator 6 when inner needle 12 is retracted into holder sleeve 1 and is constructed by side walls 1b and a top cover 1c and provided with an arrest engagement 1e for holding inner needle 12 at the rear end of holder sleeve 1 when the needle has been retracted within holder sleeve 1 and a tail plug 1d for closing the proximal end of holder sleeve 1.

As urging means 8, a coil spring is employed.

In order to facilitate connection of an outer needle hub 11a with a tube for medical liquids, the outer needle hub is formed in funnel-shape having a flange 11b at a rear 5 end thereof. As shown in FIG. 4, a filter 13 is attached inside inner needle hub 12a in order for the patient's blood not to leak out.

Formed at the near distal end portion of holder sleeve 1 is a cutout portion if, in order to facilitate handling when inner needle 12 and outer needle 11 are punctured into a patient. That is, this makes it possible for the second digit to touch inner needle hub 12a. Further, provided on the proximal side adjacent to cutout portion 1f are holding portions 1g which enable the safety indwelling needle body to be held with the first and third digits when inner needle 12 and outer needle 11 are punctured into a patient.

Inner hub 12a is fixed to actuator 6, so that inner needle 12 moves together with actuator 6 when actuator 6 is retracted. Actuating member 6a is connected to actuator 6 by a joint rod 6c arranged therebetween.

Actuating member 6a of actuator 6 has an engagement projection 6b which is inserted into an engagement window 3 formed at the near distal end portion of holder sleeve 1, so as to keep actuator 6 to the side close to outer needle 11, opposing the urging force of urging means 8.

The actuating member 6a may be formed at a front end thereof with a lift abutment 6d to which the finger is applied when the engagement projection 6b is pulled up from engagement window 3. The joint rod 6c functions as a fulcrum to the force acted on lift abutment 6d.

Engagement projection 6b and engagement window 3 are formed at such positions that the path of movement of actuating member 6a is included within the same plane that includes the axis of holder sleeve 1.

When the holding portions 1g, arranged at the front part of holder sleeve 1 on both sides of engagement window 3, are held horizontally by the first and third digits with the second digit applied perpendicularly at a position slightly forward with respect to the first and third digits, the proximal end of holder sleeve 1 abuts the palm, so that the needle tip can be fixed stably. In this position, inner needle 12 and outer needle 11 are punctured into the vein or any other blood vessel of the human body, then the flange 11b at the rear end of outer needle hub 11a is pushed out by the second digit so as to separate outer needle 11 from inner needle 12 and place the outer needle 11 into the blood vessel. Since cutout 1f is formed at the most distal end portion of holder sleeve 1, flange 11b and thereabout are adapted to be easily pushed out.

Since inner needle 12 is unsheathed after outer needle 11 has been placed into the patient, lift abutment 6d at the front part of actuating member 6a is pulled up so as to release the engagement between actuator 6 and holder sleeve 1. At this moment, the path of movement of lift abutment 6d is not a rotational motion about the axis of holder sleeve 1, so no handedness problem will occur. As pulled by coil spring 8 fixed between tail plug 1d and inner needle hub 12a, inner needle 12 is withdrawn into holder sleeve 1. Since inner needle hub 12a is fixed to the front end of actuator 6, inner needle 12 moves together with actuator 6 and is pulled backwards into holder sleeve 1.

Triangular arrest engagement 1e is formed at the near proximal end portion of slit 2. Preferably, an arrest engagement 6f is formed at the proximal end portion of actuator 6. The arrest engagement 6f of actuator 6 which has been moved by the urging force of coil spring 8 will easily pass over the arrest engagement 1e of stopper mechanism 1a. Since arrest engagement 6f and arrest engagement 1e after the former passes over the latter strike each other, the movement of actuator 6 toward the outer needle 11 side is restrained. If the storage of the inner needle can be attained by urging means 8 only, arrest engagement 6f and arrest engagement 1e are not essential. Further, though the function can be achieved by the urging means 8 only, the arrest engagement 6f and arrest engagement 1e may also be provided subsidiarily.

Figure 3:
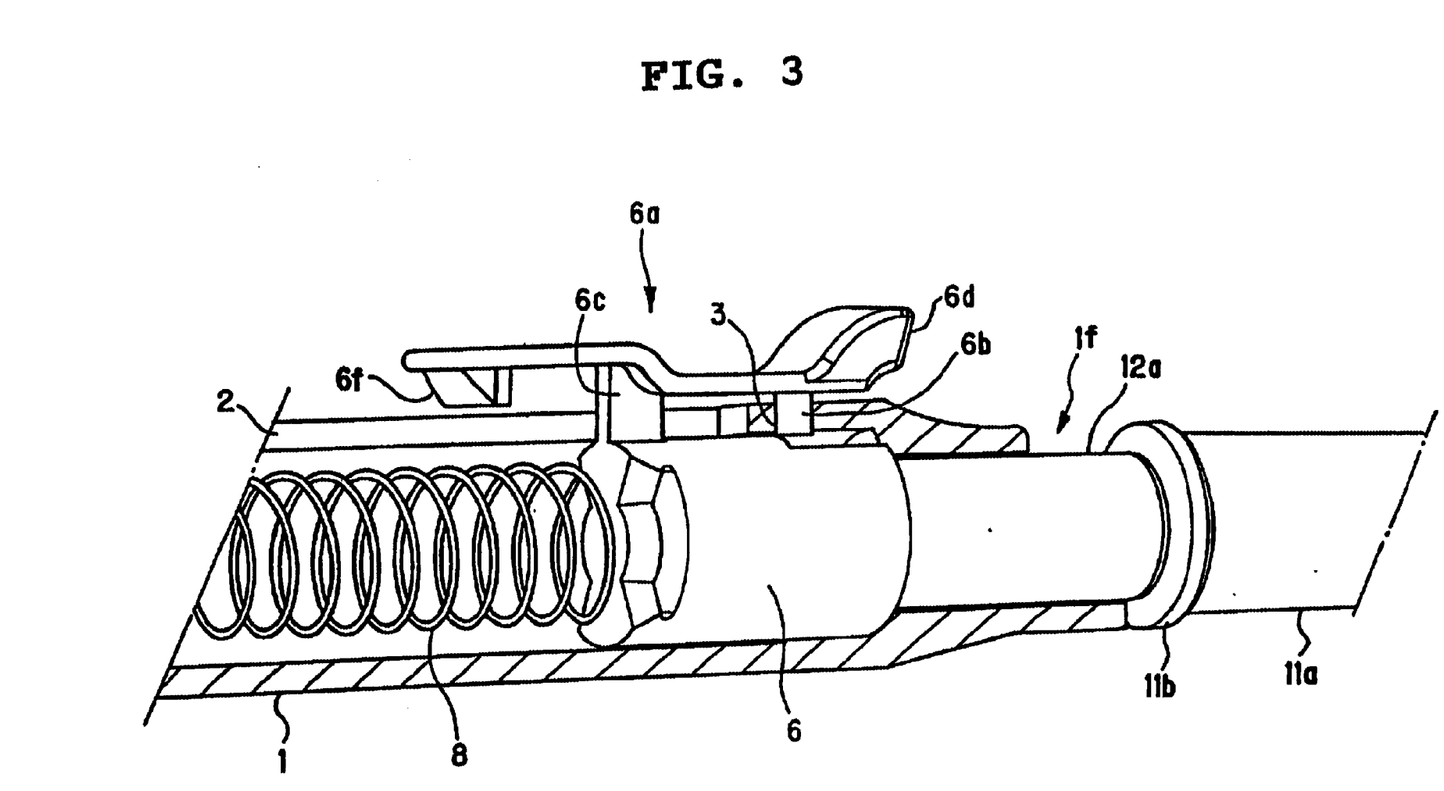
FIG. 3 is a partly enlarged, partially sectional vertical view showing an actuating member and thereabout shown in FIG. 1.

FIG. 3 shows a state before puncture into a patient.

Before inner and outer needles 12 and 11 are punctured into a blood vessel etc., engagement projection 6b of actuating member 6a has been set in engagement window 3 of holder sleeve 1. Under this condition, inner needle 12 is kept at the near distal end portion of holder sleeve 1, opposing the withdrawal tendency of inner needle 12 into holder sleeve 1 by the urging force of coil spring 8.

In order to retract inner needle 12 into holder sleeve 1 after outer needle 11 has been placed into the human body, the lift abutment 6d of actuating member 6a is pulled upwards. Then actuating member 6a rises at the front end thereof, pivoting on joint rod 6c, so that engagement projection 6b which has been fitted in engagement window 3 is pulled up. Resultantly, inner needle 12 together with actuator 6 is retracted into holder sleeve 1 by the urging force of coil spring 8.

Figure 5:
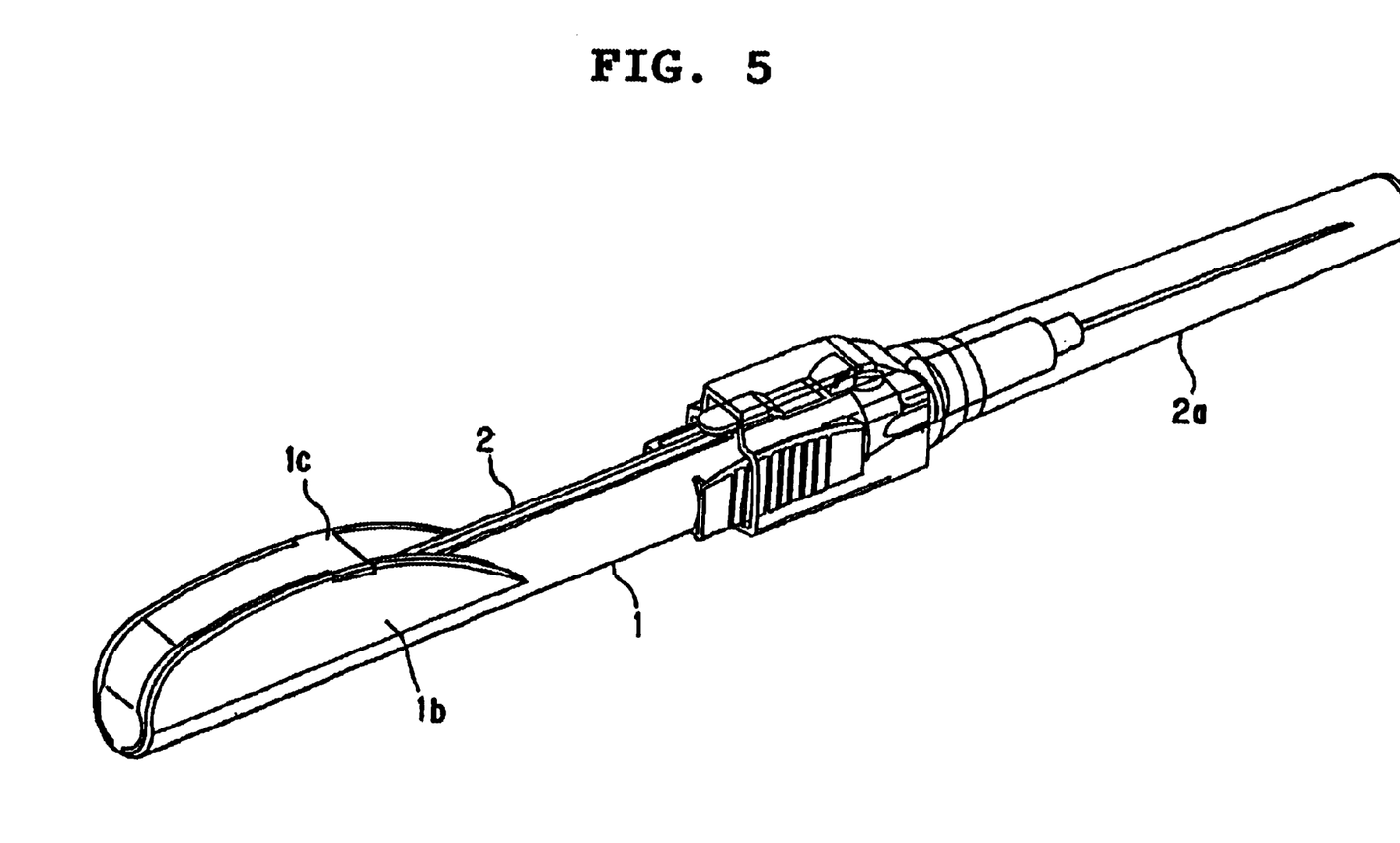
FIG. 5 is an overall perspective view showing an example of a safety indwelling needle injector with a cap fitted thereto.
Figure 6:
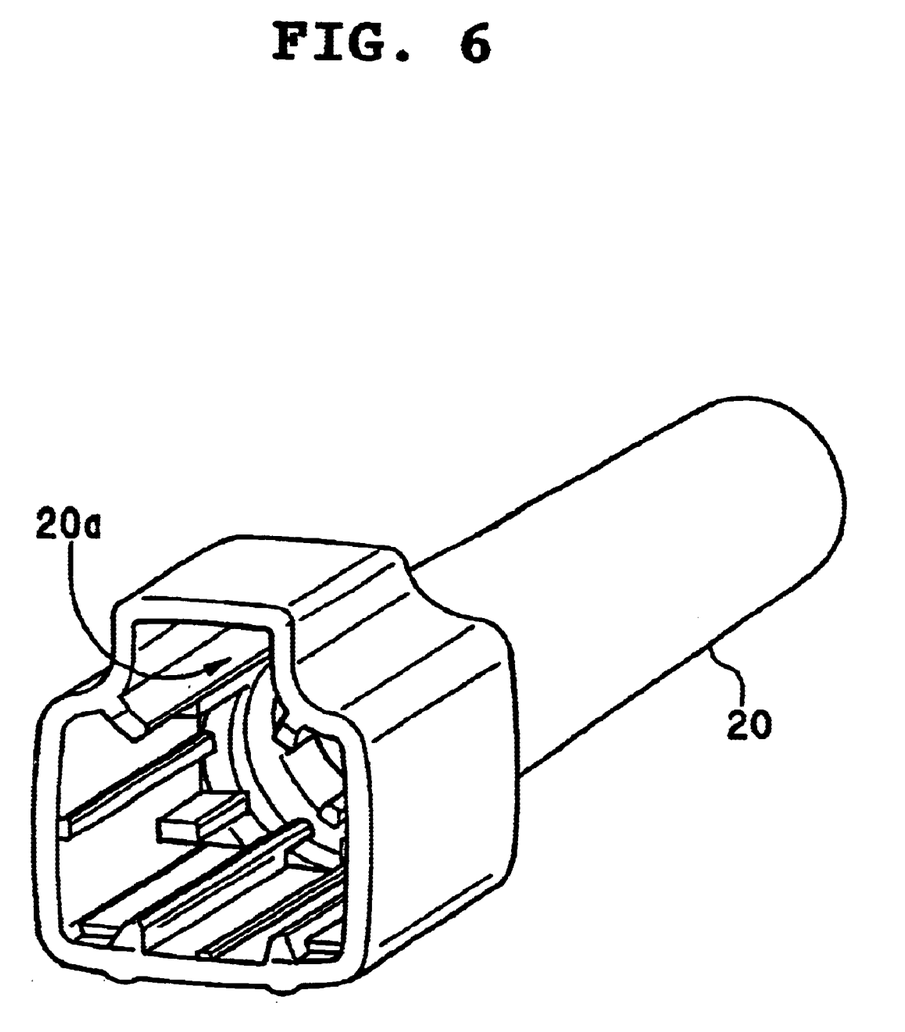
FIG. 6 is a perspective view showing a cap viewed from the opening side.

FIG. 5 shows a state where a cap 20 is fitted. FIG. 6 is a perspective view of cap 20 viewed from the opening side. Cap 20 covers outer and inner needles 11 and 12 in such a manner that they are ready for puncture and has an actuation stopper groove 20a in which actuating member 6a is fitted in an immovable manner in order to make actuating member 6a disabled. Hence, since actuating member 6a is made disabled as long as cap 20 is fitted, wrong movements such as accidental retraction of inner needle 12 into holder sleeve 1 can be prevented.

The present invention will be described with reference to another embodiment with its drawings.

Figure 7:
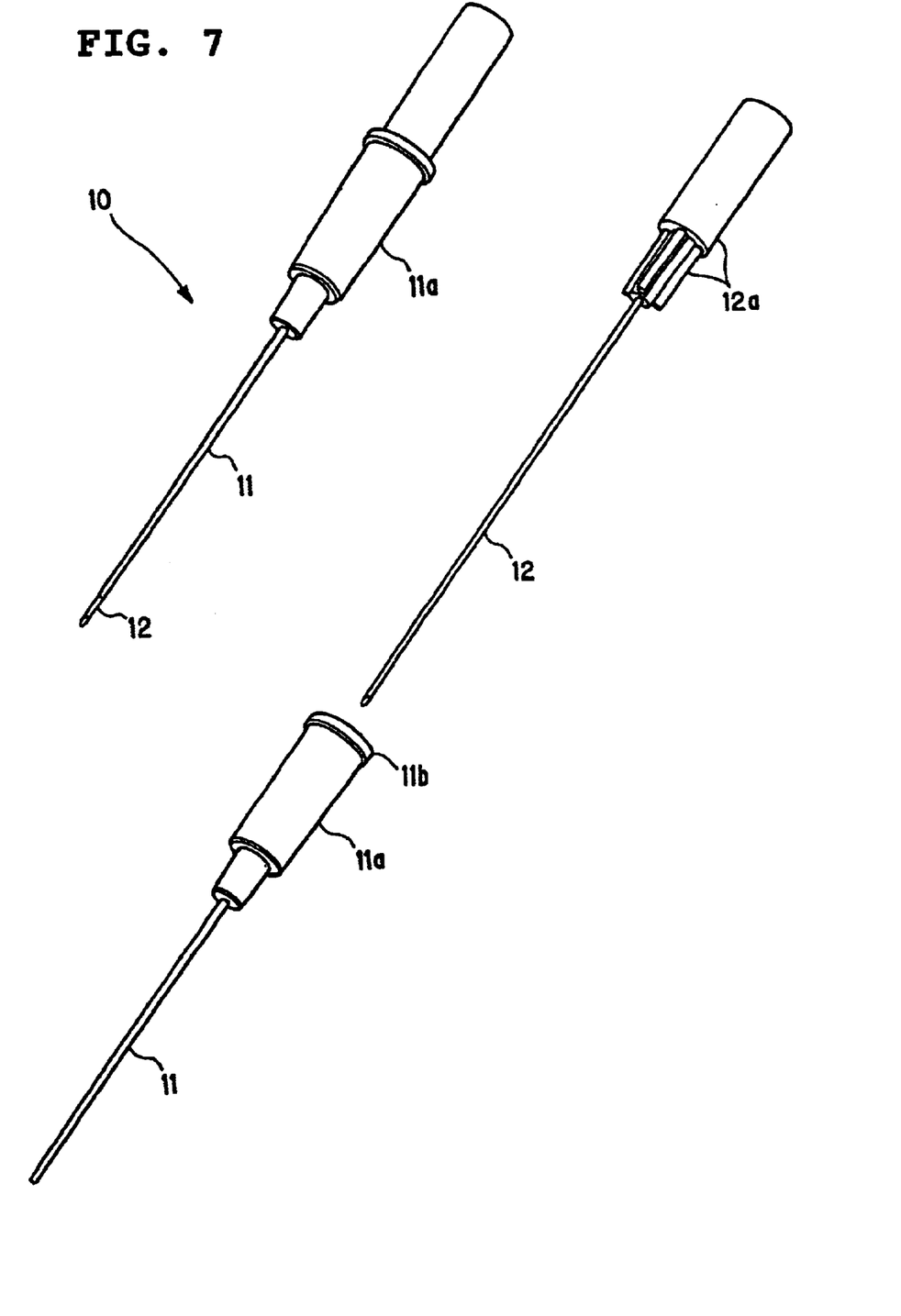
FIG. 7 is a perspective view showing a state where inner and outer needles are assembled.

The relationship between inner needle 12 and outer needle 11 is as shown in FIG. 7. As stated already, a needle structure 10 has an outer needle 11 made of a soft resin formed in pipe. This outer needle 11 has a thin-walled portion at the distal end thereof and thereby a degree of contact with inner needle 12 is increased. Provided at the proximal end of outer needle 11 is a funnel-shaped outer needle hub 11a for connection with a tube of a medical fluid such as for infusion.

With concern to the method of assembly of the safety indwelling needle injector of the present invention, actuator 6, coil spring 8 and tail plug 9 are inserted into holder sleeve 1 from a proximal end thereof. Joint rod 6c is fitted in slit 2 so that actuating member 6a is arranged on the outer side of holder sleeve 1. The actuator 6 is moved to the near distal end portion of the holder sleeve until engagement projection 6b of actuating member 6a is inserted into engagement window 3. After the insertion, inner needle 12 on which outer needle 11 is fitted is attached to actuator 6 from the distal end of holder sleeve 1.

Figure 8:
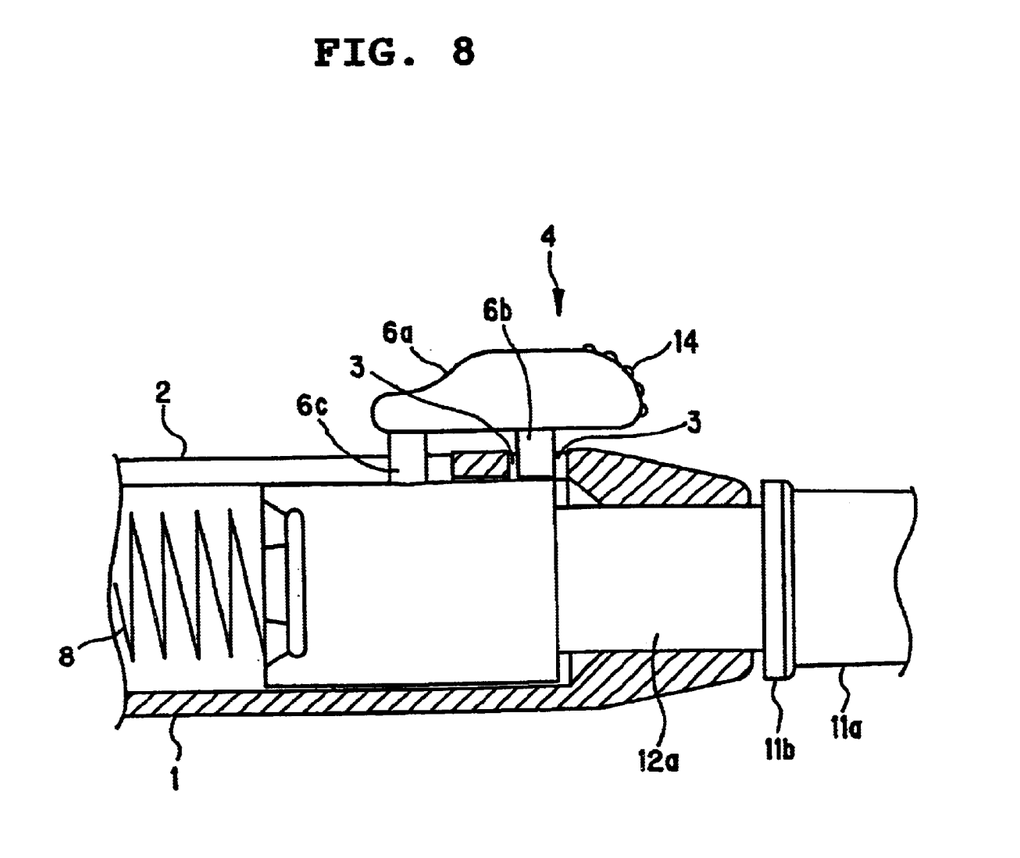
FIG. 8 is a partially sectional enlarged view showing an actuating member and thereabout according to the second embodiment.

Next, the third embodiment will be shown. In FIG. 8, joint rod 6c is attached to the proximal portion of actuating member 6a while engagement projection 6a formed at the near distal portion thereof is fitted in engagement window 3. Anti-slip ribs 14 are formed on the front side surface of actuating member 6a.

Figure 9:
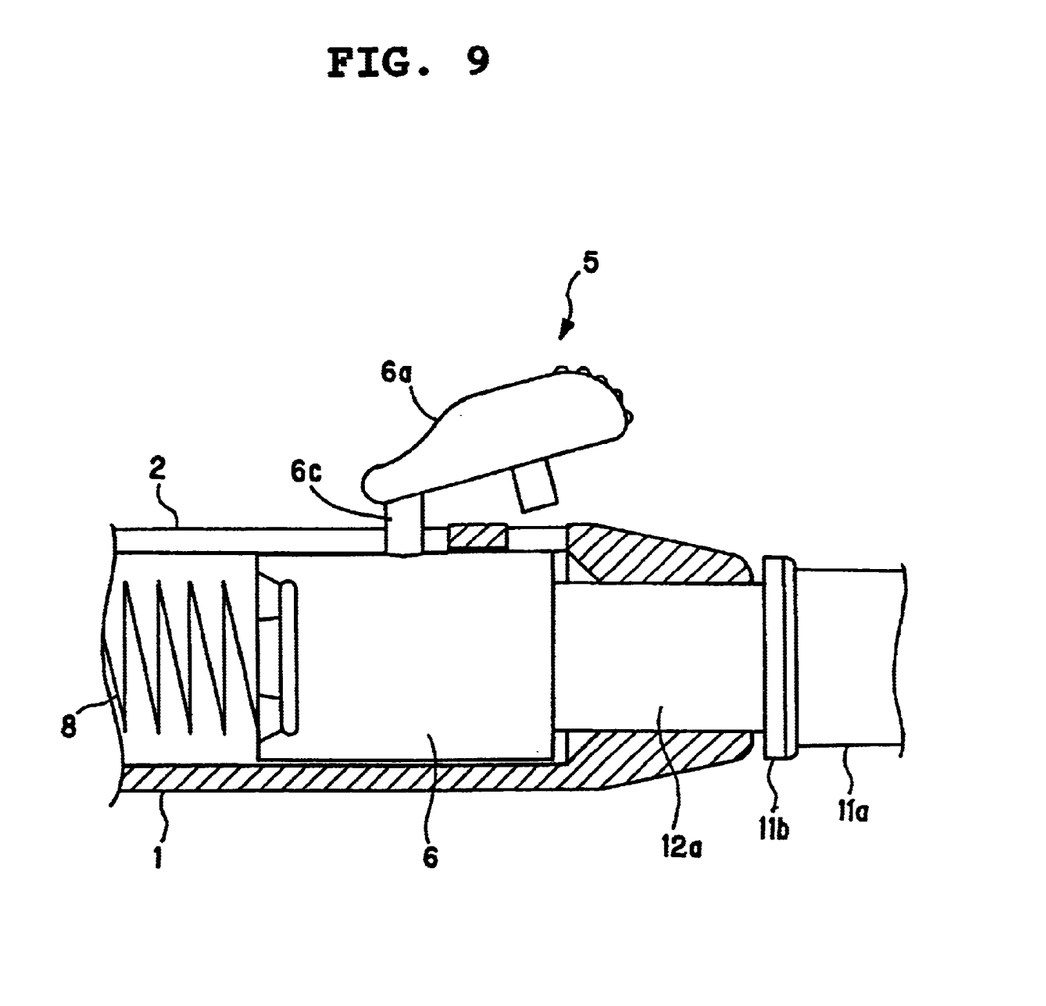
FIG. 9 is a partially sectional enlarged view showing an actuating member and thereabout according to the second embodiment.

FIG. 9 shows the released state where the insertion of actuating member 6a is disengaged. Shift from the inserted state to the released state is made by lifting the front part of actuating member 6a where anti-slip ribs 14 are formed.

Even if the fingers of the health care worker or certain items present around the health care worker abut actuating member 6a, when inner and outer needles 12 and 11 puncture, the moment of the rotational force is opposite to the moment of a force for releasing the inserted state. Therefore, the rotational moments about the fulcrum at the joint rod 6c act opposite to each other, so that the inserted state will not be released by a wrong operation. The method of assembly and other configurations are the same as in the embodiment described above.

Though this reference is common to other embodiments, it is preferred that actuator 6 and actuating member 6a should be formed of a material having elasticity. This feature makes actuating member 6a displace easily, hence release easily from the inserted state. It is also possible to join actuating member 6a and actuator 6 with another element or configure part of actuating member 6a to be fitted into engagement window 3, by a separate part.

According to the present invention it is possible to provide an indwelling needle injector configuration which is almost never actuated erroneously, free from difference in operativity depending on the handedness and easy to be assembled.

INDUSTRIAL APPLICABILITY

The safety indwelling needle according to the present invention is a safety indwelling needle comprised of a soft outer needle to be placed in a blood vessel and a hard inner needle which is fitted in the outer needle to pierce through the skin of a patient so as to introduce the outer needle into the blood vessel, and provides a suitable configuration which prevents occurrence of erroneous actuation during usage, is not different in handling depending on the handedness, and allows for easy assembly.

What is claimed is:

1. A safety indwelling needle, comprised of a soft outer needle to be inserted and placed within a blood vessel, a hard inner needle, with an inner needle hub, which is fitted in the outer needle, pierces the skin of a patient to introduce the outer needle into the blood vessel and a holder sleeve having an open distal end and a closed proximal end and capable of holding the inner needle, wherein:

the holder sleeve incorporates an urging means for urging the inner needle toward the proximal end side and an actuator which engages the inner needle at a near distal end portion of the holder sleeve so that the inner needle can be released and a tip of the inner needle is projected from the holder sleeve;

the actuator has an inner needle hub fixed at a front end thereof and is formed with an actuating member projected outside the holder sleeve;

the holder sleeve has a slit which extends to the proximal end side of the sleeve so as to hold and allow the actuating member of the actuator to slide and assures a path of movement of the actuator released from the near distal end portion of the holder sleeve; and the inner needle is adapted to be released from the holder sleeve when the actuating member, to which applied is a lifting force directing away from an axis of the holder sleeve, is moved away from the holder sleeve within a same plane that includes the axis of the holder sleeve.

2. The safety indwelling needle according to claim 1, wherein the actuating member has an engagement projection which can be fitted into an engagement window formed in the near distal end portion of the holder sleeve, and the actuator is fixed at the near distal end portion of the holder sleeve when the engagement projection is fitted in the engagement window, and the engagement between the actuator and the holder sleeve is released when the engagement projection is pulled up from the engagement window.

3. The safety indwelling needle according to claim 2, wherein the actuating member is formed to be flexible and is joined to the actuator by a joint rod located closer to the proximal end side than the engagement projection is.

4. The safety indwelling needle according to claim 3, wherein a lift abutment on which the finger is abutted when the engagement projection is pulled up from the engagement window is provided at the distal end portion of the actuating member.

* * * * *